(12) United States Patent
Iyoku et al.

(10) Patent No.: US 12,594,231 B2
(45) Date of Patent: Apr. 7, 2026

(54) EMULSIFIED COMPOSITION AND COSMETIC MATERIAL

(71) Applicant: SHIN-ETSU CHEMICAL CO., LTD., Tokyo (JP)

(72) Inventors: Hiroomi Iyoku, Annaka (JP); Shinji Irifune, Annaka (JP); Yuji Ando, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 328 days.

(21) Appl. No.: 18/275,651

(22) PCT Filed: Dec. 7, 2021

(86) PCT No.: PCT/JP2021/044907

§ 371 (c)(1),
(2) Date: Aug. 3, 2023

(87) PCT Pub. No.: WO2022/172567

PCT Pub. Date: Aug. 18, 2022

(65) Prior Publication Data

US 2024/0130954 A1     Apr. 25, 2024
US 2024/0225992 A9     Jul. 11, 2024

(30) Foreign Application Priority Data

Feb. 10, 2021     (JP) ................................. 2021-019904

(51) Int. Cl.
| | |
|---|---|
| *A61K 8/896* | (2006.01) |
| *A61K 8/06* | (2006.01) |
| *A61K 8/92* | (2006.01) |
| *A61Q 17/04* | (2006.01) |

(52) U.S. Cl.
CPC ................ *A61K 8/896* (2013.01); *A61K 8/06* (2013.01); *A61K 8/92* (2013.01); *A61Q 17/04* (2013.01)

(58) Field of Classification Search
CPC .... A61K 8/891; A61K 2800/412; A61K 8/19; A61K 8/29; A61K 2800/413; A61K 8/27; A61K 2800/623; A61K 2800/624; A61K 8/0241; A61K 2800/10; A61K 2800/33; A61K 2800/52; A61K 2800/612; A61K 2800/614; A61K 2800/651; A61K 2800/652; A61K 2800/654; A61K 8/062; A61K 8/11; A61K 8/25; A61K 8/731; A61K 8/8152; A61K 8/06; A61K 8/31; A61K 8/585; A61K 8/92; A61K 8/37; A61K 8/896; A61K 8/064; A61K 8/894; A61K 8/34; A61K 8/36; A61K 8/86; A61K 8/89; A61K 8/895; A61K 2800/43; A61K 2800/48; A61K 8/26; A61K 8/35; A61K 8/415; A61K 8/4973; A61Q 17/04; A61Q 15/00; A61Q 17/005; A61Q 19/00; A61Q 1/02; A61Q 1/04; A61Q 1/08; A61Q 1/10; A61Q 1/12; A61Q 5/06
See application file for complete search history.

(56) References Cited

U.S. PATENT DOCUMENTS

| | | | |
|---|---|---|---|
| 2009/0226609 A1 | 9/2009 | Boisvert et al. | |
| 2011/0110994 A1* | 5/2011 | Inokuchi ................ | A61K 8/891 |
| | | | 424/59 |

FOREIGN PATENT DOCUMENTS

| | | |
|---|---|---|
| CN | 101501139 A | 8/2009 |
| CN | 102061092 A | 5/2011 |
| CN | 105238071 A | 1/2016 |
| CN | 105326663 A | 2/2016 |
| JP | S61-065808 A | 4/1986 |
| JP | S61-158910 A | 7/1986 |
| JP | S62-234012 A | 10/1987 |
| JP | H11-193209 A | 7/1999 |
| JP | 2009-545649 A | 12/2009 |
| JP | 2011-102354 A | 5/2011 |

OTHER PUBLICATIONS

Inaba, R. et al., "Development of Titanium Dioxide-Containing Silicone Polymer and Applications in Cosmetics," J. Soc. Cosmet. Chem. Japan., 1999, vol. 33, No. 4, pp. 354-363.
Feb. 22, 2022 International Search Report issued in International Patent Application No. PCT/JP2021/044907.
Aug. 15, 2023 International Preliminary Report on Patentability issued in International Patent Application No. PCT/JP2021/044907.
Dec. 4, 2024 Extended European Search Report issued in European Patent Application No. 21925811.8.
May 23, 2025 Search Report issued in Chinese Patent Application No. 2021800929162.

* cited by examiner

*Primary Examiner* — Audrea B Coniglio
(74) *Attorney, Agent, or Firm* — Oliff PLC

(57) ABSTRACT

The present invention is an emulsified composition, including: (A): a titanium-atom-containing silicone resin; (B): one or more oil agents selected from the group consisting of a hydrocarbon oil, an ester oil, and a silicone oil, the oil agent being able to dissolve the component (A) and being liquid at 25° C.; and (C): water, where the emulsified composition contains no surfactant. Accordingly, an object of the present invention is to provide: an emulsified composition having excellent stability and usability without a surfactant; and a cosmetic material including the above emulsified composition and having excellent feeling of use.

4 Claims, 2 Drawing Sheets

[FIG. 2]
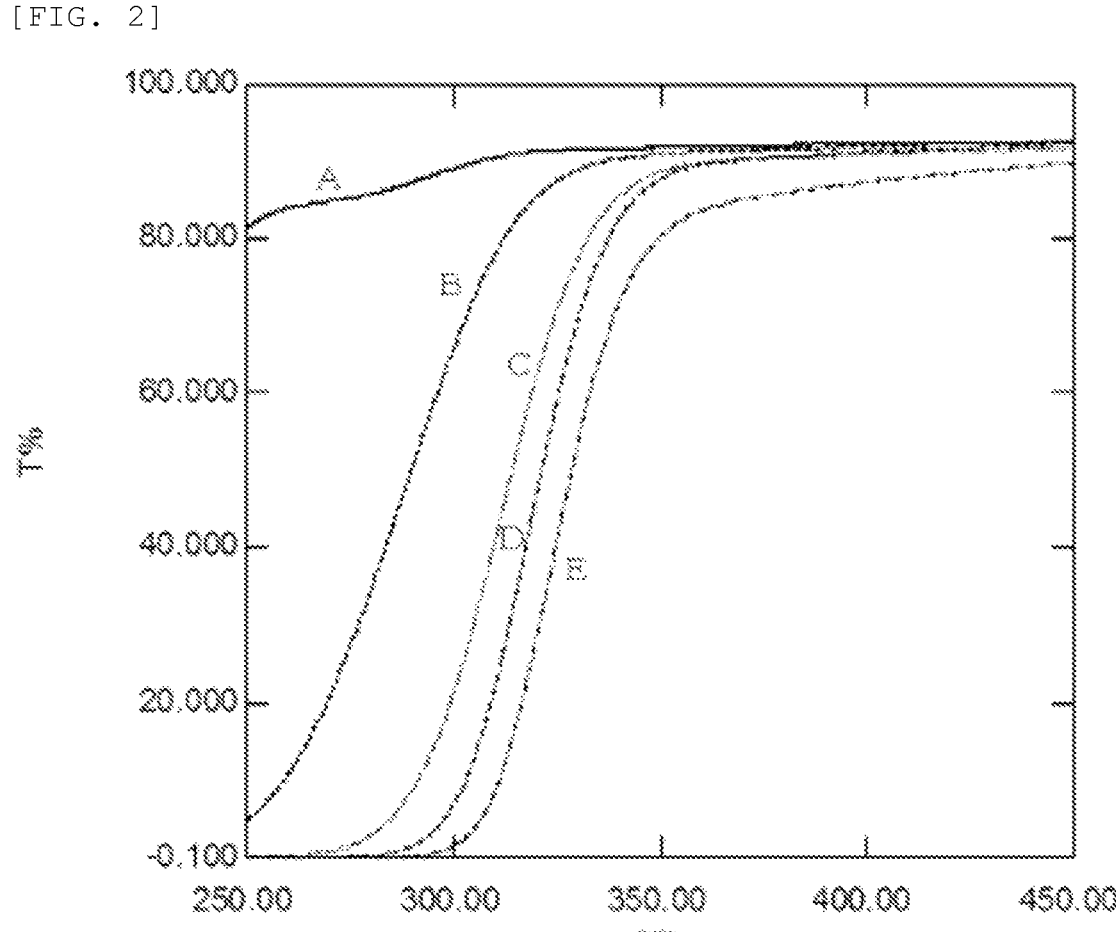

EMULSIFIED COMPOSITION AND COSMETIC MATERIAL

TECHNICAL FIELD

The present invention relates to an emulsified composition and a cosmetic material containing the emulsified composition.

BACKGROUND ART

Silicone resins, which have coating formability and excellent water resistance, sweat resistance, and sebum resistance, have been conventionally used as make-up cosmetic materials such as foundation, lipstick, eye shadow, and mascara, and raw materials for cosmetics such as a cosmetic material for protecting against ultraviolet ray and a cosmetic material for hair. For example, known are: a skin cosmetic material containing an organic silicone resin composed of a unit represented by an average formula $R_nSiO_{4-n/2}$ and a volatile hydrocarbon oil (Patent Document 1); a skin cosmetic material containing a resin composed of a $R_3SiO_{1/2}$ unit and a $SiO_{4/2}$ unit and a volatile silicone oil (Patent Document 2); and a suntan protective cosmetic material containing a silicone resin containing two or more kinds of a $R_2SiO_{2/2}$ unit, a $RSiO_{3/2}$ unit, and a $SiO_{4/2}$ unit, the terminals being optionally blocked with a $R_3SiO_{1/2}$ unit, and a volatile oil agent, where an ultraviolet-ray absorber and/or an ultraviolet-ray diffuser are blended (Patent Document 3). These materials are disclosed to yield a coating having excellent water resistance.

Furthermore, the silicone resin can form an emulsified composition with water by using a surfactant. It is well known that the silicone resin forming the emulsified composition can impart fresh and smooth touch feeling when used as a cosmetic material. Typical emulsified compositions need use of the surfactant in order to ensure temporal stability, but sliminess and tackiness derived from the surfactant are caused and improvement in feeling of use is required.

Developed in recent years is a different-metal-containing organic silicone resin having excellent water repellency and oil repellency in order to impart further functionality to the silicone resin (Patent Document 4). It is disclosed that a silicone resin containing a titanium atom has ultraviolet-ray absorbing ability, and a cosmetic material containing such a silicone resin has good adhesiveness to skin and excellent sustainability of its cosmetic effect and its effect of preventing transference. It is also suggested that the silicone resin forms an emulsified cosmetic material by using a conventional emulsifying technique, but there is a premise that "conventional emulsifying technique"="using a surfactant", and there is still the problem of feeling of use derived from the surfactant similarly to the above.

CITATION LIST

Patent Literature

Patent Document 1: JP S61-158910 A
Patent Document 2: JP S61-65808 A
Patent Document 3: JP S62-234012 A
Patent Document 4: JP H11-193209 A

SUMMARY OF INVENTION

Technical Problem

The present invention has been made in view of the above circumstances, and an object of the present invention is to provide: an emulsified composition having excellent stability and feeling of use without a surfactant; and a cosmetic material containing the emulsified composition.

Solution to Problem

To solve the above problem, the present invention provides an emulsified composition, comprising:

(A): a titanium-atom-containing silicone resin;

(B): one or more oil agents selected from the group consisting of a hydrocarbon oil, an ester oil, and a silicone oil, the oil agent being able to dissolve the component (A) and being liquid at 25° C.; and (C): water, wherein the emulsified composition contains no surfactant.

Such an emulsified composition is the emulsified composition having excellent stability and feeling of use without a surfactant.

The component (A) is preferably a titanium-atom-containing silicone resin represented by the following composition formula (1):

$$[R_3SiO_{1/2}]_a[RSiO_{3/2}]_b[SiO_{4/2}]_c[TiO_{4/2}]_d \tag{1}$$

wherein R independently represents a group selected from an alkyl group having 1 to 8 carbon atoms, an aryl group having 6 to 12 carbon atoms, and a fluorine-substituted alkyl group having 1 to 8 carbon atoms; "a" represents 0.01 to 0.7; "b" represents 0 to 0.9; "c" represents 0.01 to 0.7; "d" represents 0.01 to 0.3; and a+b+c+d represents 1.0.

When the component (A) is as above, the emulsified composition having excellent stability and feeling of use can be more easily obtained without a surfactant.

Furthermore, the emulsified composition preferably comprises 0.1 to 30.0 mass % of the component (A).

When the proportion of the component (A) is as above, emulsifying can be more easily achieved.

In addition, the present invention provides a cosmetic material comprising the above emulsified composition.

Such a cosmetic material, which contains no surfactant, can yield a cosmetic material having no sliminess nor tackiness derived from a surfactant and having excellent feeling of use when used as an emulsified cosmetic material.

Advantageous Effects of Invention

According to the present invention, an emulsified composition having excellent stability and feeling of use can be obtained without a surfactant by using a titanium-atom-containing silicone resin having a specific constituting unit. The emulsified composition can form a coating having an ultraviolet-ray absorbing effect after being applied. Furthermore, a cosmetic material having excellent feeling of use can be provided by using the inventive emulsified composition.

BRIEF DESCRIPTION OF DRAWINGS

FIG. 2 is an example of UV spectra of silicone resins synthesized in Examples and Comparative Example.

DESCRIPTION OF EMBODIMENTS

Figure 1:
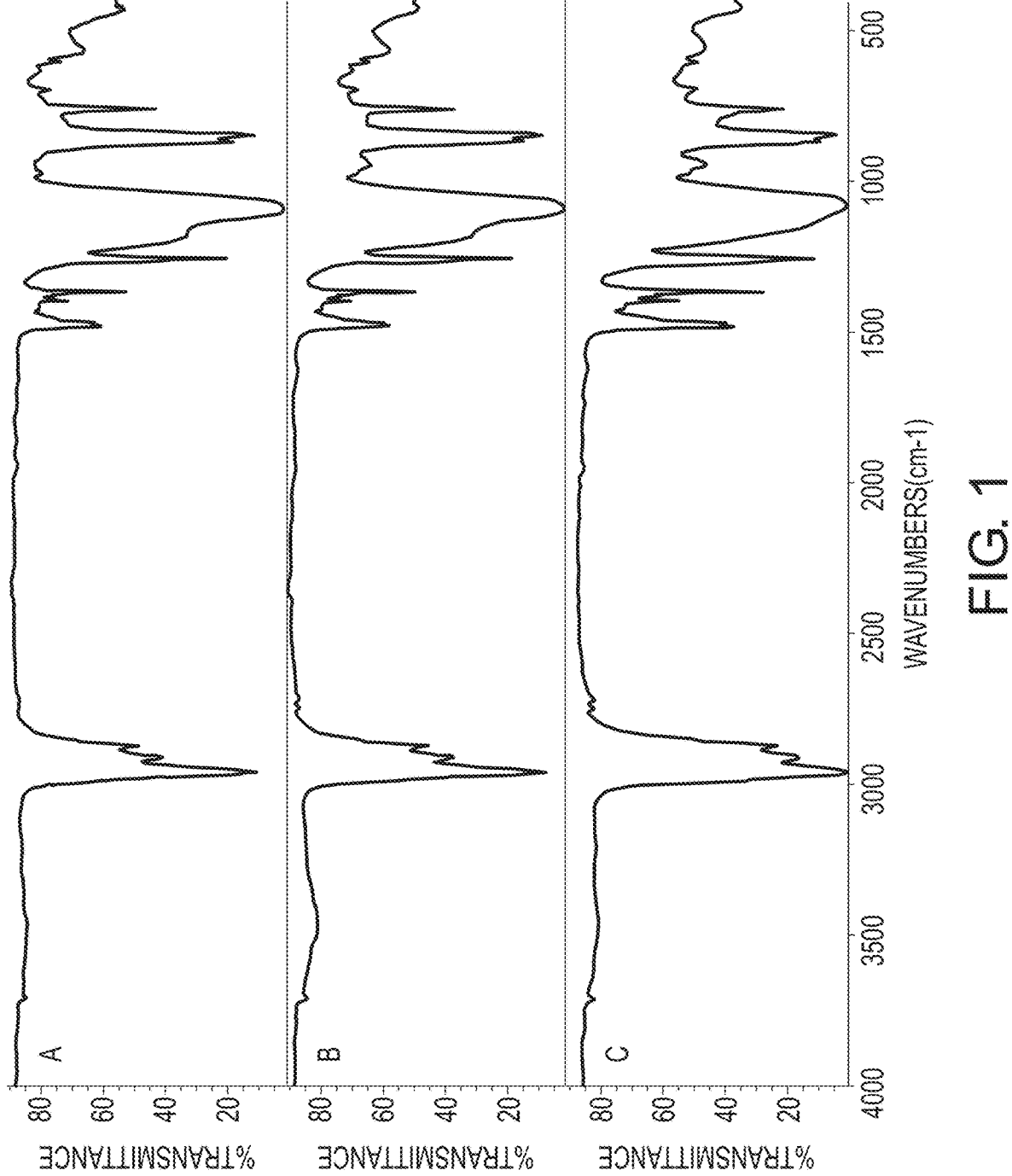
FIG. 1 is an example of IR spectra of silicone resins synthesized in Examples and Comparative Example.

As noted above, obtaining an emulsified composition having excel ent stability and feeling of use without a surfactant has been required.

The present inventors have made earnest study to solve the above problem, and consequently found that the emulsified composition having excellent stability and feeling of use can be obtained without a surfactant by using a titanium-atom-containing silicone resin having a specific constituting unit. This finding has led to complete the present invention.

Specifically, the present invention is an emulsified composition, comprising:

(A): a titanium-atom-containing silicone resin;

(B): one or more oil agents selected from the group consisting of a hydrocarbon oil, an ester oil, and a silicone oil, the oil agent being able to dissolve the component (A) and being liquid at 25° C.; and (C): water, wherein the emulsified composition contains no surfactant.

Hereinafter, the present invention will be described in detail, but the present invention is not limited thereto.

(A) Titanium-Atom-Containing Silicone Resin

The component (A) in the present invention is a titanium-atom-containing silicone resin, and specifically a silicone resin having a titanoxane unit ($TiO_{4/2}$ unit) in the molecule, for example. In particular, a titanium-atom-containing silicone resin represented by the following formula is preferable.

$$[R_3SiO_{1/2}]_a[RSiO_{3/2}]_b[SiO_{4/2}]_c[TiO_{4/2}]_d \tag{1}$$

The R independently represents a group selected from an alkyl group having 1 to 8 carbon atoms, an aryl group having 6 to 12 carbon atoms, and a fluorine-substituted alkyl group having 1 to 8 carbon atoms.

Examples of the alkyl group having 1 to 8 carbon atoms include a methyl group, an ethyl group, a propyl group, a butyl group, a pentyl group, a hexyl group, a heptyl group, and an octyl group. Examples of the aryl group having 6 to 12 carbon atoms include a phenyl group and a tolyl group. Examples of the fluorine-substituted alkyl group having 1 to 8 carbon atoms include a trifluoropropyl group.

Among them, an alkyl group having 1 to 3 carbon atoms is more preferable, and a methyl group is further preferable.

The "a" represents a number of 0.01 to 0.7, preferably 0.1 to 0.7, and more preferably 0.2 to 0.6. The "a" of 0.01 or more has no risk of gelation during manufacture, and the "a" of 0.7 or less has no risk of tackiness or liquefying of the resin coating.

The "b" represents a number of 0 to 0.9, preferably 0 to 0.8, and more preferably b=0. The "b" of 0.9 or less has no risk of gelation.

The "c" represents a number of 0.01 to 0.7, preferably 0.2 to 0.7, and more preferably 0.3 to 0.6. The "c" of 0.01 or more has no risk of tackiness or liquefying of the resin coating, and the "c" of 0.7 or less has no risk of gelation.

The "d" represents 0.01 to 0.3, preferably 0.04 to 0.2, and further preferably 0.05 to 0.15. The "d" of 0.01 or more can yield emulsifying stability more certainly, and the "d" of 0.3 or less has no risk of gelation. From the viewpoint of obtaining higher emulsifying stability, a higher value of "d" is more preferable.

About the "a", the "b", the "c", and the "d", a+b+c+d represents 1.0.

In the composition formula (1), a titanium-atom-containing silicone resin represented by the following composition formula (2) in which R represents a methyl group is particularly preferable.

$$[(CH_3)_3SiO_{1/2}]_a[CH_3SiO_{3/2}]_b[SiO_{4/2}]_c[TiO_{4/2}]_d \tag{2}$$

In the formula, "a", "b", "c", and "d" are same as above.

The titanium-atom-containing silicone resin in the present invention preferably has a weight-average molecular weight; of 500 to 20,000, more preferably 1,000 to 8,000. This range is preferable because a hard coating with good compatibility with the oil agent without tackiness can be obtained. In the present invention, the weight-average molecular weight is 3 value by gel permeation chromatography (GPC) analysis under the following conditions with polystyrene as a standard substance.

Measurement Conditions

Developing solvent: Tetrahydrofuran (THF)

Flow rate: 0.6 mL/min

Detector: Differential refractive index detector (PI)

Column: TSK Guardcolumn SuperH-H

TSKgel SuperHM-N (6.0 mmI.D.×15 cm×1)

TSKgel SuperH2500 (6.0 mmI.D.×15 cm×1)

(All the above are manufactured by Tosoh Corporation.)

Column temperature: 40° C.

Injection amount of sample: 50 μL (THF solution at a concentration of 0.3 mass %)

(B) Oil Agent

The oil agent of the component (B) is one or more oil agents selected from the group consisting of a hydrocarbon oil, an ester oil, and a silicone oil, the oil agent being able to dissolve the component (A) and being liquid at 25° C.

Examples of the hydrocarbon oil include liquid paraffin, hydrogenated polyisobutene, hydrogenated polydecene, squalane, squalene, pristane, light isoparaffin, light liquid isoparaffin, heavy liquid isoparaffin, liquid isoparaffin, tetradecene, isohexadecane, isododecane, and an α-olefin oligomer. Preferable examples thereof include isododecane.

Examples of the ester oil include ethyl oleate, ethyl linoleate, isopropyl myristate, isopropyl palmitate, isopropyl isostearate, cetyl 2-ethylhexanoate, isocetyl 2-ethylhexanoate, stearyl 2-ethylhexanoate, isostearyl 2-ethylhexanoate, cetyl palmitate, 2-ethylhexyl palmitate, 2-hexyldecyl isostearate, isostearyl isostearate, trimethylolpropane, triisostearate, myristyl myristate, cetyl myristate, octyldodecyl myristate, isostearyl, myristate, isocetyl, myristate, hexyl laurate, decyl oleate, octyldodecyl oleate, isostearyl pivalate, isopropyl isostearate, isononyl isononanoate, 2-ethylhexyl isononanoate, isodecyl isononanoate, isotridecyl, isononanoate, octyldodecyl erucate, neopentyl glycol didecanoate, pentaerythrityl tetraethylhexanoate, diisostearyl malate, trimethylcolpropane triethylhexanoate, didecyl adipate, cholesteryl isostearate, batyl isostearate, monohydroxystearic acid hydrogenated castor oil, lanolin fatty acid isostearyl ester, lanolin fatty acid isopropyl ester, lanolin fatty acid octyldodecyl ester, cetyl ricinoleate, dioctyl succinate, cetyl lactate, propylene glycol dicaprylate, propylene glycol dicaprate, propylene glycol dinonanoate, propylene glycol di(caprylate/caprate), propylene glycol diisostearate, propylene glycol dioleate, triglycerides, and animal and vegetable oils. Examples of the triglycerides include a triglyceride between: glycerin; and caproic acid, caprylic acid, capric acid, 2-ethylhexanoic acid, isotridecanoic acid, isopalmitic acid, isostearic acid, eicosanoic acid, oleic acid, etc. Examples of the animal and vegetable oils include olive oil, sunflower oil, safflower oil, castor oil, and camellia oil.

Examples of the silicone oil include: linear or branched organopolysiloxanes with from low viscosity to high viscosity, such as dimethylpolysiloxane, tristrimethylsiloxymethylsilane, caprylyl methicone, phenyl trimethicone, tetrakistrmethylsiloxysilane, meethylphenylpolysiloxane, methylhexylpolysiloxane, methylhydrogenpolysiloxane, and dimethylsiloxane-methylphenylsiloxane copolymer; cyclic organopolysiloxanes, such as octamethylcyclotetrasiloxane, decamethylcyclopentasiloxane, dodecamethylcyclo-hexasiloxane, tetramethyltetrahydrogencyclotetrasiloxane, and tetramethyltetraphenylcyclotetrasiloxane; amino-modified organopolysiloxanes; pyrrolidone-modified organopolysiloxanes; pyrrolidonecarboxylic-acid-modified organopolysiloxanes; higher-alkoxy-modified silicones, such as a stearoxysilicone; higher-fatty-acid-modified silicones; alkyl-modified silicones; long-alkyl-modified silicones; amino-acid-modified silicones; and fluorine-modified silicones.

(C) Water

The water of the component (C) is not particularly limited, and examples thereof include purified water.

Emulsified Composition

The inventive emulsified composition contains the components (A) to (C).

In the inventive emulsified composition, the components (A) and (B) form an oil layer, and the component. (C) forms an aqueous layer. The form of the inventive emulsified composition is not particularly limited, and may be an O/W emulsion, in which oil drops are dispersed in water, or may be a W/O emulsion, in which water drops are dispersed in oil, for example. In the oil layer, a ratio between the component A) and the component (B) may be uniform, or the component (A) may be unevenly distributed on a side of the oil layer surface.

A ratio between the component (A) and the component (B), which form the oil layer, is not particularly limited, but a value of the component (A): the component. (B) is preferably 0.1:19.9 to 10:10, more preferably 0.2:19.8 to 7.5:12.5, further preferably 0.5:19.5 to 5:15, and extremely preferably 1:19 to 3:17.

In the inventive emulsified composition, mass proportions of the blended components (A) to (C) are preferably as follows.

(A): 0.1 to 30 mass %, preferably 0.1 to 20 mass %, and further preferably 0.1 to 10 mass %.
  (B): 1.0 to 40 mass %, preferably 1.0 to 20 mass %, and further preferably 1.0 to 10 mass %.
  (C): 50.0 to 99.0 mass %, preferably 70.0 to 99.0, and further preferably 80 to 99.0 mass %.

The inventive emulsified composition has a feature of not containing a surfactant. The emulsified composition can be formed without a surfactant as above because of the effect of the contained titanium-atom-containing silicone resin, component (A).

<Cosmetic Material>

The inventive emulsified composition can be applied for emulsified cosmetic materials, such as moisturizing cream, emulsified foundation, suntan protective milky lotion, hair cream, and cream preparation, for example. The absence of a surfactant is preferable because there is no sliminess nor tackiness derived from a surfactant when used as these emulsified cosmetic materials, and the cosmetic material having excellent feeling of use can be obtained.

EXAMPLE

Hereinafter, Examples and Comparative Examples will be shown to specifically describe the present invention, but the present invention is not limited to the following Examples. Unless otherwise specifically described in the following examples, "%" indicates mass %. A $(CH_3)_3SiO_{1/2}$ unit is described as "M unit", a $CH_3SiO_{3/2}$ unit is described as "T unit", a $SiO_{4/2}$ is described as "Q unit", and a $TiO_{4/2}$ unit is described as "Ti unit".

Example 1

Into a reaction container, 26.18 g of hexamethyldisiloxane, 74.68 g of tetraethoxysilane, and 64 g of isopropyl alcohol (hereinafter, IPA) were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated to 90 to 115° C. for removing generated ethanol, IPA, and excess water, the mixture was cooled, then 3.96 g of tetraisopropyl orthotitanate was added dropwise with stirring, the mixture was stirred for 2 hours and then heated at 130° C. for 3 hours for removing generated IPA and water, and then cooled. Furthermore, after evaporation under a reduced pressure, the mixture was diluted with decamethylcyclopentasiloxane as an oil agent so that a concentration of the silicone resin was adjusted to be 60%, and then the mixture was filtered to obtain a 60% solution of the silicone resin in decamethylcyclopentasiloxane in which a mole ratio of M unit:Q unit:Ti unit was 0.46:0.52:0.02.

Example 2

Into a reaction container, 26.18 g of hexamethyldisiloxane, 74.68 g of tetraethoxysilane, and 64 g of IPA were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated to 90 to 115° C. for removing generated ethanol, IPA, and excess water, the mixture was cooled, then 3.96 g of tetraisopropyl orthotitanate was added dropwise with stirring, the mixture was stirred for 2 hours and then heated at 130° C. for 3 hours for removing generated IPA and water, and then cooled. Furthermore, after evaporation under a reduced pressure, the mixture was diluted with isododecane as an oil agent so that a concentration of the silicone resin was adjusted to be 60%, and then the mixture was filtered to obtain a 60% solution of the silicone resin in isododecane in which a mole ratio of M unit:Q unit:Ti unit was 0.46:0.52:0.02.

Example 3

Into a reaction container, 26.18 g of hexamethyldisiloxane, 74.68 g of tetraethoxysilane, and 64 g of IPA were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.1.3 g of calcium carbonate were added to neutralize the acid, then 100 g of isododecane was added, the mixture was heated to 90 to 115° C. for removing generated ethanol, IPA, and excess water, the mixture was cooled, then 8.08 g of tetraisopropyl orthotitanate was added dropwise with stirring, the mixture was stirred for 2 hours and then heated at 0.130° C. for 3 hours for removing generated IPA and water, and then cooled. Furthermore, after evaporation under a reduced pressure, the mixture was diluted with decamethylcyclopentasiloxane as an oil agent so that a concentration of the silicone resin was adjusted to be 60%, and then the mixture was filtered to obtain a 60% solution of the silicone resin in decamethylcyclopentasiloxane in which a mole ratio of M unit:Q unit:Ti unit was 0.46:0.50:0.04.

Example 4

Into a reaction container, 26.18 g of hexamethyldisiloxane, 74.68 g of tetraethoxysilane, and 64 g of IPA were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated to 90 to 115° C. for removing generated ethanol, IPA, and excess water, the mixture was cooled, then 8.08 g of tetraisopropyl orthotitanate was added dropwise with stirring, the mixture was stirred for 2 hours and then heated at 130° C. for 3 hours for removing generated IPA and water, and then cooled. Furthermore, after evaporation under a reduced pressure, the mixture was diluted with isododecane as an oil agent so that a concentration of the silicone resin was adjusted to be 60%, and then the mixture was filtered to obtain a 60% solution of the silicone resin in isododecane in which a mole ratio of M unit:Q unit:Ti unit was 0.46:0.50:0.04.

Example 5

Into a reaction container, 26.1.8 g of hexamethyldisiloxane, 74.68 g of tetraethoxysilane, and 64 g of IPA were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated to 90 to 115° C. for removing generated ethanol, IPA, and excess water, the mixture was cooled, then 12.37 g of tetraisopropyl orthotitanate was added dropwise with stirring, the mixture was stirred for 2 hours and then heated at 130° C. for 3 hours for removing generated IPA and water, and then cooled. Furthermore, after evaporation under a reduced pressure, the mixture was diluted with decamethylcyclopentasiloxane as an oil agent so that a concentration of the silicone resin was adjusted to be 60%, and then the mixture was filtered to obtain a 60% solution of the silicone resin in decamethylcyclopentasiloxane in which a mole ratio of M unit:Q unit:Ti unit was 0.45:0.49:0.06.

Example 6

Into a reaction container, 26.18 g of hexamethyldisiloxane, 74.68 g of tetraethoxysilane, and 64 g of IPA were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated to 90 to 115° C. for removing generated ethanol, IPA, and excess water, the mixture was cooled, then 12.37 g of tetraisopropyl orthotitanate was added dropwise with stirring, the mixture was stirred for 2 hours and then heated at 130° C. for 3 hours for removing generated IPA and water, and then cooled. Furthermore, after evaporation under a reduced pressure, the mixture was diluted with isododecane as an oil agent so that a concentration of the silicone resin was adjusted to be 60%, and then the mixture was filtered to obtain a 60% solution of the silicone resin in isododecane in which a mole ratio of M unit:Q unit:Ti unit was 0.45:0.49:0.06.

Example 7

Into a reaction container, 23.27 g of hexamethyldisiloxane, 74.68 g of tetraethoxysilane, and 64 g of IPA were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated to 90 to 115° C. for removing generated ethanol, IPA, and excess water, the mixture was cooled, then 15.97 g of tetraisopropyl orthotitanate was added dropwise with stirring, the mixture was stirred for 2 hours and then heated at 130° C. for 3 hours for removing generated IPA and water, and then cooled. Furthermore, after evaporation under a reduced pressure, the mixture was diluted with isododecane as an oil agent so that a concentration of the silicone resin was adjusted to be 60%, and then the mixture was filtered to obtain a 60% solution of the silicone resin in isododecane in which a mole ratio of M unit:Q unit:Ti unit was 0.41:0.51:0.08.

Example 8

Into a reaction container, 26.18 g of hexamethyldisiloxane, 12.78 g of triethoxymethylsilane, 59.75 g of tetraethoxysilane, and 64 g of IPA were added, 0.64 g of methanesulfonic acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated to 90 to 115° C. for removing generated ethanol, IPA, and excess water, the mixture was cooled, then 21.54 g of tetraisopropyl orthotitanate was added dropwise with stirring, the mixture was stirred for 2 hours and then heated at 130° C. for 3 hours for removing generated IPA and water, and then cooled. Furthermore, after evaporation under a reduced pressure, the mixture was diluted with isododecane as an oil agent so that a concentration of the silicone resin was adjusted to be 60%, and then the mixture was filtered to obtain a 60% solution of the silicone resin in isododecane in which a mole ratio of M unit:T unit:Q unit:Ti unit was 0.43:0.09:0.38:0.10.

Comparative Example 1

Into a reaction container, 26.18 g of hexamethyldisiloxane, 74.68 g of tetraethoxysilane, and 64 g of IPA were added, 0.64 g of methanesulfonic acid was added thereinto, and the mixture was cooled to 10 to 20° C. and 47.54 g of added, the mixture was heated at 130° C. for 3 hours for removing generated ethanol, IPA, and excess water, and cooled. Furthermore, after evaporation under a reduced pressure, the mixture was diluted with isododecane as an oil agent so that a concentration of the silicone resin was adjusted to be 60%, and then the mixture was filtered to obtain a 60% solution of the silicone resin in isododecane in which a mole ratio of M unit:T unit:Q unit was 0.47:0.05:0.48.

The following Table 1 shows the mole ratio of the constituting units, refractive index, kinematic viscosity, etc. of each silicone resin obtained in the above examples. The following refractive index and viscosity are respectively values measured as the resin solution at a concentration shown in the Table.

TABLE 1

| | Composition (mole ratio) | | | | Refractive index | resin concentration (%) | Kinematic viscosity $(mm^2/s)$ | Oil agent |
|---|---|---|---|---|---|---|---|---|
| | M | T | Q | Ti | | | | |
| Ex. 1 | 0.46 | — | 0.52 | 0.02 | 1.411 | 60 | 920 | D5 |
| Ex. 2 | 0.46 | — | 0.52 | 0.02 | 1.421 | 60 | 50 | ID |
| Ex. 3 | 0.46 | — | 0.50 | 0.04 | 1.414 | 60 | 1900 | D5 |
| Ex. 4 | 0.46 | — | 0.50 | 0.04 | 1.424 | 60 | 55 | ID |
| Ex. 5 | 0.45 | — | 0.49 | 0.06 | 1.418 | 60 | 4500 | D5 |
| Ex. 6 | 0.45 | — | 0.49 | 0.06 | 1.427 | 60 | 80 | ID |
| Ex. 7 | 0.41 | — | 0.51 | 0.08 | 1.430 | 60 | 150 | ID |
| Ex. 8 | 0.43 | 0.09 | 0.38 | 0.10 | 1.433 | 60 | 541 | ID |
| Comp. Ex. 1 | 0.47 | — | 0.53 | — | 1.417 | 60 | 30 | ID |
| Comp. Ex. 2 | 0.47 | 0.05 | 0.48 | — | 1.415 | 60 | 20 | ID | water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was added, the mixture was heated at 130° C. for 3 hours for removing generated ethanol, IPA, and excess water, and cooled. Furthermore, after evaporation under a reduced pressure, the mixture was diluted with isododecane as an oil agent so that a concentration of the silicone resin was adjusted to be 60%, and then the mixture was filtered to obtain a 60% solution of the silicone resin in isododecane in which a mole ratio of M unit:Q unit was 0.47:0.53.

Comparative Example 2

Into a reaction container, 26.18 g of hexamethyldisiloxane, 6.39 g of triethoxymethylsilane, 67.23 g of tetraethoxysilane, and 64 g of IPA were added, 0.64 g of methanesulfonic: acid was added thereinto, and the mixture was cooled to 10 to 20° C. and 47.54 g of water was added dropwise with stirring. After the dropwise addition, the mixture was heated at 50 to 80° C. for 5 hours for performing hydrolysis and condensation reactions to obtain a silicone resin solution.

Subsequently, 1.03 g of a 25% aqueous solution of sodium hydroxide and 0.13 g of calcium carbonate were added to neutralize the acid, then 100 g of isododecane was The mole ratio of the composition was calculated from the ratio of the prepared raw materials.

The refractive index was a value ($n^D$) at 25° C. measured by using an Abbe's refractometer described in JIS K 0062:1.992.

The kinematic viscosity was a value at 25° C. measured by using a Cannon-Fenske viscosimeter described in JIS Z 8803:2011.

D5: Decamethylcyclopentasiloxane

ID: Isododecane

Infrared-Ray-Absorbing Characteristics

By using an infrared spectrometer Nicolet iS50 manufactured by Thermo Scientific Inc.), each of the silicone resin solutions obtained in Examples and Comparative Examples was applied on a KBr cell to measure an IR spectrum. FIG. 1 shows the measurement results. A is the IR spectrum of Comparative Example 1, B is that of Example 4, and C is that of Example 7.

In Examples 4 and 7, which blended the titanium-atom-containing silicone resin, a peak derived from Ti—O—Si (near 945 $cm^{-1}$) was observed. This peak was not able to be detected in Comparative Example 1, which blended the silicone resin containing no titanium atom.

Ultraviolet-Ray Absorbing Characteristics

Each of the silicone resin solutions obtained in Examples and Comparative Examples was diluted with isopropanol so that the silicone resin concentration was 1 g/L, and an UV spectrum of the diluted solution was measured by using an ultraviolet spectrometer UV-2200 (manufactured by SHIMADZU CORPORATION) with a quartz-glass cell with 10 mm in thickness. FIG. 2 shows the measurement results. A is the result of the UV spectrum of Comparative Example 1, B is that of Example 2, C is that of Example 4, D is that of Example 6, and E is that of Example 7.

It has been confirmed that a larger content of the titanium atoms in the resin increases the ultraviolet ray absorbability. Since the titanium-atom-containing silicone resin has the ultraviolet ray absorbability, applying the emulsion obtained with the titanium-atom-containing silicone resin as the emulsifier can yield a coating film having an ultraviolet-ray blocking, effect.

Emulsifying Characteristics

The emulsifying characteristics were observed by using the silicone resin solutions obtained in the above examples. Table 2 shows the blended amounts.

TABLE 2

| Blended amount (g) | Resin concentration (%) | | |
| | 5 | 3 | 1 |
| --- | --- | --- | --- |
| Resin | 5 | 3 | 1 |
| *Oil agent | 15 | 17 | 19 |
| Water | 80 | 80 | 80 |
| Total | 100 | 100 | 100 |

*The oil agent is the oil agent used for the solution during the resin synthesis.

Each of the silicone resins and the oil agents were taken in a container, the mixture was stirred by using HOMOGENIZING DISPER (manufactured by PRIMIX Corporation) at 500 rpm for 1 minute, and then water was gradually added with stirring. After the addition of water, the mixture was stirred at 1,000 rpm for 5 minutes to produce an emulsion. The emulsion was placed in a constant-temperature dryer at 25° C. to be left overnight, and stability of the emulsion was visually observed. Table 3 shows the results.

TABLE 3

| | Resin concentration (%) | | |
| | 5 | 3 | 1 |
| --- | --- | --- | --- |
| Example 1 | Uniform | Uniform | Uniform |
| Example 2 | Uniform | Uniform | Uniform |
| Example 3 | Uniform | Uniform | Uniform |
| Example 4 | Uniform | Uniform | Uniform |
| Example 5 | Uniform | Uniform | Uniform |
| Example 6 | Uniform | Uniform | Uniform |
| Example 7 | Uniform | Uniform | Uniform |
| Example 8 | Uniform | Uniform | Uniform |
| Comparative Example 1 | Separated | Separated | Separated |
| Comparative Example 2 | Separated | Separated | Separated |

TABLE 3-continued

| | Resin concentration (%) | | |
| | 5 | 3 | 1 |
| --- | --- | --- | --- |
| Polyether-modified silicone (Note 1)/ID | Uniform | Separated | Separated |
| Alkyl-modified-crosslinked polyether-modified silicone (Note 2) | Uniform | Separated | Separated |

(Note 1)
KF-6017, manufactured by Shin-Etsu Chemical Co., Ltd.
(Note 2)
KSG-320, manufactured by Shin-Etsu Chemical Co., Ltd.

Comparative Examples 1 and 2, which used the silicone resin containing no titanium atom, failed to yield an emulsion. However, Examples 1 to 8, which used the titanium-atom-containing silicone resin, yielded the emulsion, and yielded the emulsified composition without an emulsifier. It has been further found that the amount of the resin required for emulsification decreases and the emulsifying ability increases as the titanium atom content increases. In addition, Examples had higher emulsifying ability than the polyether-modified silicone, which was a silicone-based emulsifier.

Emulsified compositions were prepared by using the titanium-atom-containing silicone resin solutions obtained in the above examples to evaluate the feeling of use (tackiness), Evaluation of Feeling of Use The emulsified composition obtained with the following blending table 5 was evaluated by 50 specialized female panelists regarding spread (spreading property) during coating, feeling of tackiness, and refreshing feeling with evaluation criteria shown in the following Table 4. An average of the evaluation results was calculated.

TABLE 4

| Points | Spread | Feeling of tackiness | Refreshing feeling |
| --- | --- | --- | --- |
| 5 | Good | None | Good |
| 4 | Somewhat good | Almost none | Somewhat good |
| 3 | Average | Normal | Average |
| 2 | Somewhat poor | Slightly tacking | Somewhat poor |
| 1 | Poor | Tacking | Poor |

Table 5 shows the results based on the average of the obtained evaluation results based on the following.

Excellent: The average was 4.0 points or more.

Good: The average was 3.0 points or more and less than 4.0 points.

Fair: The average was 2.0 points or more and less than 3.0 points.

Poor: The average was less than 2.0 points.

TABLE 5

| No. | Blended amount (g) | Ex. 9 | Ex. 10 | Ex. 11 | Comp. Ex. 3 |
| --- | --- | --- | --- | --- | --- |
| 1 | Silicone resin solution of Example 6 | 2 | | | |
| 2 | Silicone resin solution of Example 7 | | 2 | | |
| 3 | Silicone resin solution of Example 8 | | | 2 | |

TABLE 5-continued

| No. | Blended amount (g) | Ex. 9 | Ex. 10 | Ex. 11 | Comp. Ex. 3 |
|---|---|---|---|---|---|
| 4 | Polyoxyethylene hydrogenated castor oil (PEG-10) | | | | 1.2 |
| 5 | Decamethylcyclopentasiloxane | 18.8 | 0 | 0 | 0 |
| 6 | Isododecane | | 18.8 | 18.8 | 18.8 |
| 7 | 1,3-Butylene glycol | 5 | 5 | 5 | 5 |
| 8 | Sodium chloride | 0.5 | 0.5 | 0.5 | 0.5 |
| 9 | Antiseptic | 0.5 | 0.5 | 0.5 | 0.5 |
| 10 | Purified water | 73.2 | 73.2 | 73.2 | 73.2 |
| Feeling of use | Absence of tackiness | Excellent | Excellent | Excellent | Poor |
| | Goodness of spread | Excellent | Excellent | Excellent | Poor |
| | Refreshing feeling | Excellent | Excellent | Excellent | Poor |

As obvious from Table 5, the inventive cosmetic material was excellent in all the evaluation points compared with Comparative Example.

Therefore, it has been found that the emulsified composition having the feeling of use without tackiness can be obtained by using the titanium-atom-containing silicone resin.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. An emulsified composition, comprising:

(A): a titanium-atom-containing silicone resin;

(B): one or more oil agents selected from the group consisting of a hydrocarbon oil, an ester oil, and a silicone oil, the oil agent being able to dissolve the component (A) and being liquid at 25° C.; and (C): water, wherein the emulsified composition contains no surfactant, and wherein the component (A) is a titanium-atom-containing silicone resin represented by the following composition formula (1):

$$[R_3SiO_{1/2}]_a[RSiO_{3/2}]_b[SiO_{4/2}]_c[TiO_{4/2}]_d \qquad (1)$$

wherein R independently represents a group selected from an alkyl group having 1 to 8 carbon atoms, an aryl group having 6 to 12 carbon atoms, and a fluorine-substituted alkyl group having 1 to 8 carbon atoms; "a" is from 0.01 to 0.7; "b" is from 0 to 0.9; "c" is from 0.01 to 0.7; "d" is from 0.01 to 0.3; and a+b+c+d is 1.0.

2. The emulsified composition according to claim 1, wherein the emulsified composition comprises 0.1 to 30.0 mass % of the component (A).

3. A cosmetic material, comprising the emulsified composition according to claim 1.

4. A cosmetic material, comprising the emulsified composition according to claim 2.

* * * * *